(12) United States Patent
Bacaud et al.

(10) Patent No.: US 6,497,844 B1
(45) Date of Patent: Dec. 24, 2002

(54) MICROPILOT-TYPE EQUIPMENT FOR CATALYTIC TESTING PROCESS

(75) Inventors: Robert Bacaud, Lyons (FR); Michel Ageron, Rilleux la Pape (FR); Laurence Renaudin, Caluire (FR); Michel Vrinat, Caluire (FR); Didier Letourneur, Briand (FR); Slavik Kasztelan, Rueil Malmaison (FR)

(73) Assignee: Institut Francais du Petrole, Rueil Malmaison (FR)

( * ) Notice: Subject to any disclaimer, the term of this patent is extended or adjusted under 35 U.S.C. 154(b) by 0 days.

(21) Appl. No.: 09/298,922

(22) Filed: Apr. 26, 1999

(30) Foreign Application Priority Data

Apr. 24, 1998 (FR) .............................. 98 05284

(51) Int. Cl.⁷ .............................................. G01N 31/10
(52) U.S. Cl. .................... 422/68.1; 422/78; 422/80; 436/37
(58) Field of Search .................... 436/37; 422/68.1, 422/78, 80, 101

(56) References Cited

U.S. PATENT DOCUMENTS 4,099,923 A  *  7/1978  Millberger 6,086,832 A  *  7/2000  Ohta

FOREIGN PATENT DOCUMENTS

| DE | 24 25 227 | 3/1975 |
| FR | 2 529 472 | 1/1984 |
| FR | 2 583 519 | 12/1986 |

OTHER PUBLICATIONS

XP–002089402, Vrinat, "A New High Pressure Flow Microreactor for Rapid Evaluation of Heterogeneous Catalysts", ACTAS Simp. Iberoam. Catal., 9th, vol. 2, No. 11, 1984, pp. 1637–1638.

XP–002089401, Vrinat et al., "A Flow Microreactor for Laboratory High Pressure Vapor Phase Catalytic Reactions", React. Kinet. Catal. Lett., vol. 14, No. 4, 1980, pp. 389–394. (1980).

* cited by examiner

Primary Examiner—Jan Ludlow
(74) Attorney, Agent, or Firm—Millen, White, Zelano & Branigan, P.C.

(57) ABSTRACT

The invention relates to equipment for pretreatment of catalysts and/or catalytic testing that makes it possible to establish the material balance of a chemical reaction in the presence of very small amounts of solid catalyst under operating conditions of industrial use.

14 Claims, 1 Drawing Sheet

MICROPILOT-TYPE EQUIPMENT FOR CATALYTIC TESTING PROCESS

The invention relates to equipment for pretreatment of a catalyst and/or for micropilot-type catalytic testing that make it possible to establish the material balance of a chemical reaction in the presence of very small amounts of solid catalyst. It also relates to a process for pretreatment of catalysts and/or catalytic testing that is implemented in the equipment according to the invention.

The invention also relates to the use of the equipment according to the invention to solve problems that are associated with the use of catalysts in the areas of refining, petrochemistry, treatment or conversion of gas, or fine chemistry.

The evaluation of the performances of new solids in heterogeneous catalysis in reactions for converting liquid feedstocks in the presence of gaseous reagents should be carried out under a wide range of experimental conditions (pressure, flow rates, temperature, concentrations of reagents). The length of time that it takes to carry out the complete testing of a solid depends on, on the one hand, the dwell time of the reagents in contact with the catalyst, and, on the other, run-up times between each modification of the value of an experimental parameter.

The measurements of catalytic activity on a laboratory scale are frequently made in the gaseous phase on model substances that represent reactions under study. The study of the activity of small amounts of catalysts in the presence of industrial feedstocks that comprise at least one liquid product is generally done only in a batch reactor (autoclave). Very often, the amount of catalyst that is needed to carry out a test on a pilot unit which usually uses a catalyst volume of 20 to 1000 $cm^3$ and whose reactor has a volume that is generally greater than 50 $cm^3$ is not available.

The design of the small pilot installations (micropilot-type equipment) that are intended for the evaluation of the performance of new catalytic formulations in the conversion of liquid feedstocks relies on the miniaturization of industrial pilot units. The equipment generally comprises reactors that can hold several cubic centimeters of catalyst. The flows of reagents, liquid feedstock, and reactive gas are regulated with elements such as metering pumps and regulating valves. The separators that ensure the distribution of gaseous and liquid effluents are based on, as for the pilot units, the regulation of a liquid level. The order of magnitude of the dwell time of the feedstock in the reactor can be very high since the reactivity of the feedstock is low or the harshness of the treatment is increased. Thus, the hourly volumetric flow rates on the order of 2 $h^{-1}$ are commonly used. Such values, compared to the volumes of the reactors and systems for separation and collection, consequently have run-up times on the order of several days. The evaluation of the activity of a catalyst should cover a wide range of reaction conditions, which involves frequent variation of the operating parameters of the reactor (pressure, flow rates, temperature). A long regulating period after each modification of the value of one of these magnitudes severely penalizes the productivity of such an installation.

The applicant, who is confronted with the need for carrying out a number of catalytic activity tests under conditions that are identical to those of the industrial reactors, developed micropilot-type equipment and a process for testing and collecting samples for analysis that make it possible to obtain a quick response to each evaluation experiment. This purpose of the equipment and of the process according to the invention is achieved by a reduction of the run-up times that are associated with the small sizes and with the very small amount of catalyst, as well as by forced automation, compared to the pilots and test processes that are mentioned above. The equipment and the process according to the invention thus make it possible to collect samples of liquid or gaseous effluents that are separated after reaction for the purposes of complementary analyses, if necessary, unlike the equipment that is described in French Patents 2 583 519 and 2 529 472, all the while establishing material balances around a chemical reaction.

This invention therefore relates in particular to equipment for pretreatment of catalysts and/or for catalytic testing that makes it possible to draw up the material balance of a chemical reaction and therefore to evaluate the transformation of mixtures of liquid and gaseous products, in the presence of very small amounts of solid catalyst, in particular in granular or divided form, under operating conditions (reaction temperature, pressure, time of contact) of industrial use.

Figure 1:
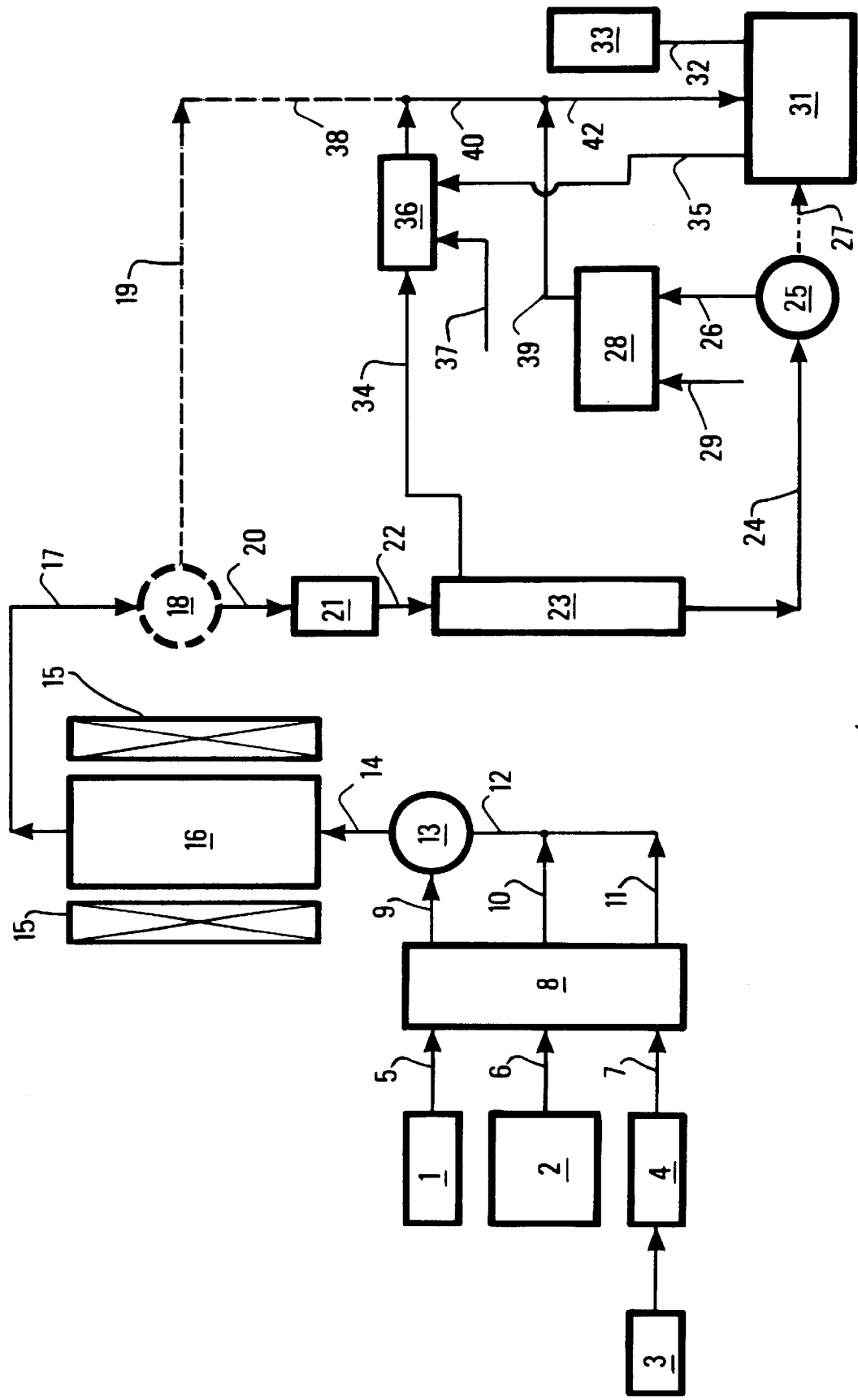
FIG. 1 depicts a special embodiment of the equipment according to the invention.

The miniaturized equipment, with optimized dimensions, essentially comprises:

a reactor 16 that has a volume of generally between 0.1 and 20 $cm^3$, preferably between 0.5 and 5 $cm^3$, into which the catalyst is placed, at least one system for injecting into the reactor at least one-liquid or liquid mixture 4 and/or at least one system for injecting at least one gas or gas mixture 2, and/or at least one gas or gas mixture 1 that is necessary for the pretreatment of the catalyst, via a switching valve 13, means for regulating and/or measuring the flow rate and composition of said liquid or liquid mixture, and said gas and/or gas mixture (8), at least one means for heating 15 said liquid or liquid mixture and/or said gas or gas and said liquid mixture before their entry into the reactor or preferably in the reactor, optionally at least one switching valve 18 that ensures the transfer of liquid and gaseous effluents from the reactor either to at least one condensation means 21 and/or separation means 23, or optionally to a preferably pressurized reservoir 31, at least one means for condensation 21 and/or separation 23 of liquid and/or gaseous effluents after or at the time of their condensation, whereby the volume of said means is generally between 0.1 and 20 $cm^3$, preferably between 0.5 and 5 $cm^3$, and in which the liquid level and the sampling of gaseous effluents are managed by at least one valve 25 and at least one regulation sequence that alternately ensures the accumulation of the liquid phase in separator 23, its transfer to a sample collector 28, or optionally to a preferably pressurized reservoir 31, at least one collector of samples of liquid effluents 28 and at least one collector of samples of gaseous effluents 36 that comprise or are associated with means for measuring the volumes of liquid and gas that are collected, at least one pressure regulation means 33 that ensures a constant pressure in all of the zones that comprise the reaction section (supply, reactor) and the section where the means of condensation, separation, and sampling are located and preferably connected to reservoir 31.

It is also possible to use a single means for carrying out the condensation and separation of the effluents from the reactor preferably separator 23. These elements are connected to one another via lines that ensure the circulation of the reagents and/or the products and that can be arranged according to the particular scheme that is indicated in FIG. 1. This equipment makes it possible to obtain results of tests and/or pretreatments that are reliable and that can be reproduced industrially in a very limited length of time by an implementation that is simplified and is therefore more economical. The equipment that essentially consists of this set of elements can also be used for the pretreatment of catalysts with or without analysis of the effluents that are obtained from the reactor during pretreatment, according to a process that is presented in detail later.

Reactor 16 consists of a pipe that receives at least one catalyst in the form of powder or grain of a size that is generally smaller than 6 mm, in various forms, such as, for example, extrudates. The volume of the reactor is generally between 0.1 and 20 cm$^3$, preferably between 0.5 and 5 cm$^3$, its inside diameter D is generally between 1 and 30 mm, preferably between 3 and 15 mm, more preferably between 4 and 8 mm, and its length L is generally between 1 and 1000 mm, preferably between 5 and 500 mm, more preferably between 50 and 120 mm, such that the L/D ratio is greater than 2. L/D is preferably greater than 10, and more preferably L/D is greater than 15. Furthermore, the L/D ratio can generally reach any value that is greater than 2, but more preferably it is less than 45 and even more preferably less than 40. The reactor can operate at a pressure between atmospheric pressure and 35 Mpa, preferably at a pressure between 1 and 25 MPa, and at a temperature of between 20 to 800° C., preferably between 20 and 650° C. In the reactor, the catalyst is placed between two deactivated alumina layers (100–200 mesh). The amount of catalyst that is used is generally between 0.01 and 15 cm$^3$, preferably between 0.1 and 10 cm$^3$, and more preferably between 0.2 and 2 cm$^3$. The sintered metal filters hold the entire catalytic bed and ensure the filtering of the effluent.

Reactor 16 is preferably placed in a heating means 15, such as, for example, a furnace that consists of a light alloy shell that surrounds the reactor as well as its inlet and outlet connectors. Heating is preferably ensured by heating elements that are clamped in the shell; the length of these resistors is greater than that of the reactor, and their distribution around the axis of the furnace ensures a uniform temperature profile along the axis of the reactor over a length that is greater than that which the catalytic bed occupies. The regulation thermocouple is optionally and preferably inserted into a radial glove finger that is located in the center of the catalytic bed.

Reactor 16 is fed with liquid preferably via a pressurized reservoir 3 via a liquid injection means 4, such as, for example, a pump. This liquid may be an inert solvent, or a reactive liquid or a mixture of reactive liquids, or a liquid or liquid mixture that can be used to pretreat the catalyst, or else a mixture of solvent and/or reagents and/or liquids for pretreatment. The gaseous reagents are supplied by, for example, pressurized cylinders that are equipped with a pressure regulator. The flows of liquid reagents 4 and gas reagents 2 and/or gas reagents and/or liquid reagents for pretreatment 1 are introduced respectively in lines 7, 6, and 5, and then controlled with regulating means and/or flow rate measuring means 8. They are then admitted into the inlet of the reactor via, for example, one or more T-shaped connectors that connect lines 10 and 11 to line 12, then via switching valve 13 that makes it possible to admit into the reactor, via line 14, either the mixture for pretreatment that is obtained from line 9, or the liquid or liquid mixture that is obtained from line 11 and/or the gas or gas mixture that is obtained from line 12. The liquid flow rate is generally between 0 and 100 g·h$^{-1}$, preferably between 0.1 and 90 g·h$^{-1}$, and more preferably between 1 and 20 g·h$^{-1}$. The gas flow rate is generally between 0 and 5000 cm$^3$·min$^{-1}$, preferably between 0.1 and 500 cm$^3$·min$^{-1}$, and more preferably between 1 and 50 cm$^3$·min$^{-1}$. The circulation of the fluids in the reactor can take place from bottom to top or from top to bottom.

At the outlet of the reactor, after condensation in a condenser 21, the products are collected via line 22 in a separator 23 with an inside diameter that is generally between 1 and 30 mm, preferably between 3 and 15 mm, and more preferably between 2 and 8 mm; and with a length that is generally between 1 and 1000 mm, preferably between 5 and 500 mm, and more preferably between 40 and 100 mm; whose volume is generally between 0.1 and 20 cm$^3$, and preferably between 0.5 and 5 cm$^3$. This pipe acts as, on the one hand, a liquid and gaseous phase separator and, on the other, as a reservoir for the periodic collection of a defined liquid volume. It is also possible and preferred to condense the effluents from the reactor in separator 23; this makes it unnecessary to use a separate condenser 21.

A switching valve 18 optionally can be placed between reactor 16 and condenser 21. This valve optionally makes it possible to direct the effluents directly from the reactor to reservoir 31 via lines 19, 40, and 42. This is useful, for example, when pretreatment of the catalyst is carried out that does not require analysis of the effluents of the reactor.

A switching valve 25 that is connected to separator 23 via line 24 alternately ensures the accumulation of the liquid phase in separator 23 or its sequential transfer to a sampling loop and a sample collector that is included in 28, via line 26.

The separator can preferably be reduced to a simple pipe, generally without a system for detecting the liquid level; this considerably simplifies this equipment. The sampling of liquid is carried out without disrupting the operational speed of the reactor. The contents of the loop are periodically transferred into the receiving pipes of a sample collector 28, where it is degassed by a stream of inert gas. The samples that are thus collected can then be analyzed by any technique that is suitable for the reaction in question, such as, for example, liquid or gas chromatography, infrared, ultraviolet, or mass spectrometry, or else X-fluorescence.

Excess liquid is optionally evacuated via line 27 to a preferably pressurized reservoir 31 with a capacity that is preferably almost identical to that of supply reservoir 3, which also collects the gaseous phase. The pressure of all of the sections, i.e., the reaction section (supply, reactor) and the section where the means for condensation, separation and sampling are located, is kept at a constant value with a pressure regulating means 33 such as, for example, a regulating valve that is associated with a pressure sensor. The pressure regulating means can be located anywhere that makes it possible to maintain the desired pressure in reactor 16, condenser 21, separator 23 and collectors 28 and 36. In particular, it can be located right in front of reservoir 31 when said reservoir is not pressurized.

The collection of gaseous samples in collector 36 can be done either from separator 23, via line 34, or from reservoir 31 via line 35, or via these two lines simultaneously. Gas collectors 36 or liquid collectors 28 can be fed by inert gas via, respectively, lines 29 and/or 37 to keep these samples protected from air and/or to purge the equipment at the end of pretreatment and/or a test. After collection, the samples of collectors 28 and 36 can be evacuated via lines 38 and 29, and then 40 and 42, to reservoir 31.

The flows of gas and liquid are preferably regulated and measured with means of mass flow rate regulation. This preferred selection of a single technique for the control of various flow rates provides the advantage of simplification and standardization of the control and regulation circuits. It ensures a constant pulsation-free flow rate for the liquid and makes it unnecessary to resort to high-pressure, complex, expensive, and delicate pumps.

The regulation of the values of the flow rates of reagents, pressure, and temperature is ensured preferably by regulators with proportional, integral, and differential self-adapting action. The set-point values can be transmitted by, for example, an RS485-type connection.

The selection of the supply: gas or liquid that is reactive or necessary for the pretreatment of the catalyst, as well as switching valve 18 that make it possible to choose among three equipment operating modes:

1) test of the catalyst (or catalytic test) with separation of the liquid and gaseous phases,
2) pretreatment of the catalyst with separation of the liquid and gaseous phases
3) pretreatment of the catalyst without separation of the liquid and gaseous phases.

In the first operating mode of the equipment according to the invention, it is possible to carry out a catalytic test, followed by an analysis of effluents that are condensed in condenser 21 and separated in separator 23.

In the second mode, it is possible to carry out pretreatment of the catalyst, followed by an analysis of the effluents that are condensed in condenser 21 and separated in separator 23.

In the third mode, pretreatment of the catalyst is carried out, but the analysis of the liquid and gaseous effluents that are obtained from the reactor is not desired. It is thus not necessary to condense and/or to separate said effluents, which are therefore sent directly to reservoir 31 via lines 19, 40, and 42, without passing through condenser 21 and/or separator 23. It is also possible to carry out successively a pretreatment (mode 2 or 3) and then a catalytic test (mode 1), whereby the liquid and gaseous effluents that are separated are optionally analyzed both during pretreatment (mode 2) and during the catalytic test (mode 1), whereby modes 2 and 1 are used one after the other.

Switching valve 13 makes it possible to select the type of gas or gas mixture that is admitted into the reactor: pretreatment gas 1 or gas or gas mixture for carrying out reaction 2.

The switching and closing valves are controlled by pneumatic actuators that are controlled by solenoid valves. Filling of pressurized reservoir 3 can be ensured by, for example, a sampling pump from a reagent drum.

Liquid sample collector 28, which also contains a sampling loop, can optionally receive up to 100 pipes, preferably 5 to 100 pipes that preferably contain 0.1 to 20 cm$^3$, and more preferably 0.5 to 5 cm$^3$ of liquid product.

In the event of failure of a regulating element (thermocouple, regulating valve, pressure sensor), the regulators cancel the set-point value. An overheating safety cuts the power supply to the furnace. It is advantageous and therefore preferred to equip the reactive circuits with plugs and nonreturn valves.

To simplify the equipment, valves 13 and/or 18 and/or 25 can optionally be combined into a single multichannel valve or two multichannel valves that are preferably located upstream from the reactor and/or the condenser and separator.

The invention also relates to equipment for the pretreatment of catalysts. It is actually possible to use the equipment according to the invention for initiating catalyst pretreatment under operating conditions of industrial use.

The invention also relates to a catalytic testing process that makes it possible to evaluate the transformation of a feedstock of known composition and flow rate and that comprises at least one liquid product and/or at least one gaseous product, and injected into the reactor in the presence of small amounts of catalyst, and under operating conditions of industrial use, characterized in that it is implemented in the equipment according to the invention and in that it comprises the following successive stages:

a) Selection of the operating mode of the equipment that corresponds to the production of a catalytic test (mode 1)

b) Supplying of the reactor with at least one liquid and/or at least one gas, whereby the reactor is operated at the desired temperature and pressure.

c) Condensation of at least a portion of the effluents of the reactor.

d) Separation of the liquid and gaseous effluents that are obtained in stage c).

e) Measurement of the volumes of liquid and gaseous effluents that are separated in stage d) for a given time interval.

f) Sequential transfer of the liquid that is obtained in stage e) in a sampling loop, then in a liquid sample collector.

g) Transfer of excess liquid to an optionally pressurized reservoir.

h) Taking at least one sample of the gaseous phase that is separated in stage d).

i) Analysis of at least one liquid sample that is obtained in stage f) and at least one gaseous phase sample that is taken in stage h).

Stages c) and d) of the process according to the invention can be successive or simultaneous.

The volumes of the effluents can be determined by any means that is known to one skilled in the art, for example, by weighing in the case of the liquid effluents and with a gas counter in the case of the gaseous effluents.

The samples of the gaseous and liquid phases can be analyzed (stage i) by any means that are known to one skilled in the art, for example by gas chromatography.

The invention also relates to a process for pretreatment of a catalyst under industrial operating conditions, characterized in that it is implemented in the equipment according to the invention and in that it comprises the following successive stages:

a) Selection of the operating mode of the equipment corresponding to the pretreatment of the catalyst without separation of the liquid and gaseous phases (mode 3)

b) Supplying of the reactor with at least one liquid and/or at least one gas, whereby the reactor is operated at the desired temperature and pressure.

c) Sending the effluents from the reactor to an optionally pressurized reservoir.

The invention also relates to a process for pretreatment of a catalyst under industrial operating conditions, characterized in that it is implemented in the equipment according to the invention and in that it comprises the following successive stages:

a) Selection of the operating mode of the equipment that corresponds to: pretreatment of the catalyst with separation of the liquid and gaseous phases (mode 2).

b) Supplying of the reactor with at least one liquid and/or at least one gas, whereby the reactor is operated at the desired temperature and pressure.

c) Condensation of at least a portion of the effluents of the reactor.

d) Separation of the liquid and gaseous effluents that are obtained in stage c).

e) Measurement of the total volume of the liquid and gaseous effluents that are separated in stage d) during a given time interval.

f) Sequential transfer of the liquid that is obtained in stage d) into a liquid sample collector.

g) Transfer of excess liquid to an optionally pressurized reservoir.

To track the pretreatment of the catalyst with analyses of gaseous and liquid phases, it is optionally possible to produce, according to stage f), the following additional stages:

h) Taking of at least one sample of the gaseous phase that is separated in stage d).

i) Analysis of at least one liquid sample that is obtained in stage f) and at least one gaseous phase sample that is taken in stage h).

The pretreatment of the catalyst can consist of, for example, reduction, for example, with pure hydrogen or with a gas mixture that contains hydrogen, or gaseous phase sulfurization with gas or gas mixture (1) that contains a sulfurized compound, such as, for example, hydrogen sulfide ($H_2S$) or a hydrogen/hydrogen sulfide ($H_2/H_2S$) mixture and/or in the liquid phase with a liquid or a liquid mixture, for example a mixture of hydrocarbons and dimethyl disulfide (DMDS) that is placed in reservoir 3, optionally combined with gas or gas mixture 1, at the same pressure or at a pressure that is different from that of the reaction. When the pretreatment precedes a catalytic test in the same reactor, it can optionally be carried out at a pressure that is different from that of the reaction.

The elements (reservoir filling pump, collector, valves, regulators, measuring systems) are preferably connected by different interfaces to a computer. The control software ensures the sequential course of experiments and the recording of the operations. The main functionalities of the program are:

1. Control of the various elements: this operating mode makes it possible for the operator to control the valves, the regulators, and the collection of samples for the purpose of developing new programming sequences.

2. Acquisition of regulation parameters and characteristic physical magnitudes of the reactor (volume of the separator, nature of the reagents, . . . ).

3. Programming of sequences: the structure of the program takes into consideration an experiment such as the course of i measurement sequences that are carried out with a catalyst by using the variable parameters of pressure, flow rates, temperature, and number of samples. The parameters that are selected by the operator make it possible to calculate set-points that are transmitted to regulators during the cycle of the experiment.

4. Starting of a program: a preferred cycle consists of, for example, the course of the following operations:
   4.1. Initialization:
   Transmission of starting set-points to the regulators
   Positioning of the valves
   4.2 Pretreatment of the catalyst
   4.3 Filling of the reservoir with liquid reagent
   4.4 Pressurization of the reaction circuit
   4.5 Loop of i sequences that comprise taking n samples
   4.6 End of the reaction
   Emptying of the pipes of the liquid sample collector, depressurization, shut-down.

During the experiment, the set-points that are transmitted to the regulators, as well as the real values of the corresponding parameters are recorded by the program. At the end of the experiment, a file that contains all of the data on its course can be exploited with computer software (spreadsheet).

The control software ascertains the compatibility of the parameters that are programmed by the operator with the characteristics of the device. During an experiment, the software compares the values of the measured magnitudes to the set-points. The persistence of a deviation that exceeds a predetermined threshold causes a shutdown sequence to be implemented. During the experiment, it is possible to interrupt the program with a function key. This request should be confirmed to obtain the execution of the end of experiment mode.

The technical choices that are made result in a reduction in investment and in operating costs thanks to, on the one hand, the small amounts of catalysts and reagents that are used and, on the other, the quickness of the regulation.

The equipment according to the invention is particularly well suited for solving many problems that are associated with the use of catalysts in the areas of refining, petrochemistry or gas conversion or fine chemistry. The invention can be used for multiple applications. These applications can be selected from, for example, the group that consists of: hydrogenation, hydrocracking, hydrotreatment, hydroisomerization, reforming, catalytic cracking, transformation of aromatic compounds (isomerization, dismutation, hydrodealkylation), dehydrogenation, partial or total oxidation, the transformation of synthesis gas into methanol, into higher alcohols, or into hydrocarbons (Fischer-Tropsch synthesis), and the conversion of methanol into hydrocarbons.

The equipment and the processes according to this invention make it possible, for example, to carry out the following studies:

Evaluation of the performance of catalysts in terms of activity, selectivity, deactivation, and thermal stability.

Determination of the influence of the operating parameters (pressure, temperature, dwell time) on the activity and selectivities.

Comparison of the performances of different catalysts.

Kinetic studies.

Research of the optimal pretreatment and use conditions in the industrial unit.

The prototype that was produced in the laboratory made it possible to carry out the development of the equipment. The studies that relate to the material transfer dynamics made it possible to delimit the operating range of the reactor. The validation of the complete equipment (supplies, regulations, reactor, condensation, separation, collection of samples) then was done by measuring the activity of several reference catalysts in the area of hydrotreatment of a gas oil fraction, with equipment according to the invention, followed by an analysis by chromatography of the samples that are collected.

As an example, the evaluation of the activity of a catalyst can be done in 24 hours, and the complete determination of the kinetic parameters in a gas oil hydrodesulfurization reaction (order, speed constant, activation energy) is done in less than one week.

The results that are obtained were compared to those that are obtained during the hydrotreatment of the same feedstock and in the presence of the same catalysts, in a conventional pilot unit whose reactor has a volume of 180 cm³.

The comparison of the results that are obtained with the two techniques confirmed the validity of the activity measurements conducted on the micropilot according to the invention and the speed of the evaluation of the activity of a catalyst. The examples below illustrate the effectiveness of the equipment and processes according to the invention.

EXAMPLES

Example 1

Tests of Reference Catalysts in the Hydrodesulfurization of Gas Oil on an Industrial Pilot Three hydrodesulfurization catalysts, an NiMo/alumina (catalyst A), a CoMo alumina (catalyst B), and a CoMO/alumina with a low Co and Mo content (catalyst C) were tested with regard to the hydrodesulfurization of a gas oil in the industrial pilot. The main characteristics of the gas oil are indicated in Table 1.

TABLE 1

Characteristics of the Gas Oil

| | |
|---|---|
| Density at 15° C. | 0.849 g/cm³ |
| Sulfur | 1.32% by mass |
| Total nitrogen | 89 mg/liter |
| Distillation (% by vol) | |
| PI | 229.2° C. |
| 10% | 265.7° C. |
| 50% | 308° C. |
| 90% | 368.6° C. |
| 95% | 383° C. |

In this first example, the industrial pilot reactor that has a volume of 180 cm³ was charged with an amount of catalyst of 25 cm³. The catalyst is sulfurized by the feedstock, to which 2% by weight of dimethyl disulfide (DMDS) was added. The sulfurization of the catalyst is carried out at a VVH of 67 h⁻¹ by raising the temperature from ambient temperature to 320° C., at a temperature rate of 10°C./minute. This temperature was then maintained for 5 hours.

The test is then performed by injecting pure feedstock and by regulating the temperature to the selected value. The experimental conditions that are used for the test on the industrial pilot are as follows:

VVH=2 h⁻¹

H2/liquid ratio=150 1/1

Hydrogen pressure=3 MPa

Reaction temperature=between 300° C. and 390° C.

Total pressure between 3 and 3.6 MPa (according to the temperature).

TABLE 2

| | HDS Conversion (%) | | | | | |
|---|---|---|---|---|---|---|
| | Catalyst A | | Catalyst B | | Catalyst C | |
| Temperature in ° C. | Micro-pilot | Industrial pilot | Micro-pilot | Industrial pilot | Micro-pilot | Industrial pilot |
| 330 | — | — | 77.4 | 77.0 | 73.1 | 73.6 |
| 360 | 93.1 | 93.3 | 91.0 | 91.7 | 89.3 | 89.1 |
| 390 | 98.5 | 98.6 | 97.8 | 98.0 | 96.9 | 96.7 |
| Length of time | 24 h | 100 h | 36 h | 120 h | 36 h | 120 h |

The results, expressed by conversion during desulfurization, are presented in Table 2. The HDS conversion is defined as the total percentage of sulfur that is contained in the feedstock and is eliminated by the catalytic treatment essentially in the form of H₂S in the gaseous effluent. The values are given at approximately 0.2%.

$$\text{HDS conversion (\%)} = \frac{So \times Vo - Sl \times Vl}{So \times Vo} \times 100$$

where

Vo is the volume of gas oil that is introduced

Vl is the total volume of liquid effluent that is obtained from the separator

So is the percentage of sulfur in the feedstock

Sl is the percentage of sulfur in the liquid

So and Sl are determined by X-fluorescence analysis of the liquid.

Example 2

Tests of the Reference Catalysts in Hydrodesulfurization of Gas Oil on Micropilot Three catalysts A, B, and C of Example 1 were tested with the micropilot according to the invention. To reproduce the operating conditions that are used for the industrial pilot-scale tests of Example 1, a catalyst volume of 0.6 cm is used in the micropilot of the invention and loaded into reactor 16 with a volume that is equal to 4 cm³.

The catalysts are sulfurized in the micropilot that is operated in mode 3 by the feedstock that is placed in reservoir 3, to which 2% by weight of dimethyl disulfide (DMDS) was added. The sulfurization is carried out at a VVH of 6 h-1by raising the temperature from ambient temperature to 320° C., at a temperature increase rate of 10° C./minute using furnace 15. This temperature is then maintained for 1 hour. The effluents that are obtained from the reactor are sent directly to pressurized reservoir 31.

The micropilot is then operated according to mode 1, which makes it possible to carry out a catalytic test by injecting with a pump 4 the pure feedstock that is placed in reservoir 3 and by regulating the temperature to the value that is selected. The experimental conditions are those that are used for the test on the industrial pilot and are regulated with flow regulators 8 and pressure regulators 33:

VVH=2 h-1 (liquid flow rate of 1.8 g/h)

H2/liquid ratio=150 1/1

Hydrogen pressure=3 MPa

Reaction temperature=between 300° C. and 390° C.

Total pressure of between 3 and 3.6 MPa (according to the reaction temperature).

At the outlet of the reactor, the products are collected in a pipe that acts both as condenser 21 and as liquid and gaseous phase separator 23. This pipe has an inside diameter of 3 mm and a length of 50 mm. Switching valve 25 alternately ensures the accumulation of the liquid phase in condenser/separator 23 or its sequential transfer into a liquid sample collector 28, where it is degassed by a stream of inert gas. These liquid phase samples are analyzed by gas chromatography or X-fluorescence chromatography.

Excess liquid is evacuated to a pressurized reservoir 31, which also collects the gaseous phase. Gaseous phase samples are collected via gaseous sample collector 36 and are analyzed by gas chromatography. A material balance is drawn up from liquid and gaseous phase analyses and liquid and gaseous feedstock flow rates.

The comparison between the conversions that are obtained in the pilot reactor and measured with the micropilot on the three reference catalysts is presented in Table 2.

There is a very good consistency between the results that are obtained in the micropilot and those of the industrial pilot. Under experimental conditions that are identical to those used during the measurements on the industrial pilot, it is therefore verified that the classification of the three reference catalysts is reproduced. Furthermore, it will be noted that the time that it takes to acquire these results is considerably shorter with the micropilot of the invention, as the values of the length of time of the test in Table 2 show.

Example 3

Sulfurization of a Catalyst

Catalyst A is loaded into reactor 16 of the micropilot according to the invention that is operated according to mode 3. It is then sulfurized with a mixture of hydrogen and hydrogen sulfide (H2S) that contains 2% by weight of H2S via the injection system of a gas mixture for pretreatment 1. The sulfurization is carried out at atmospheric pressure and at a VVH of 6 h-1 by raising the temperature from ambient temperature to 320° C., at a temperature increase rate of 10° C./minute. This temperature is maintained for one hour. The effluents that are obtained from the reactor during the pretreatment are sent directly to pressurized reservoir 31. The unit is then allowed to cool to ambient temperature, and then the catalyst is unloaded for purposes of analysis. The sulfur content of the pretreated catalyst is 7.8% S.

What is claimed is:

1. Equipment for pretreatment of a catalyst and/or for catalyst testing that makes it possible to draw up the material balance of a chemical reaction in the presence of very small amounts of solid catalyst under operating conditions of industrial use which comprises:

a reactor (16), capable of containing a catalyst at least one system for injecting into said reactor at least one fluid comprising liquid or liquid mixture (4), optionally at least one system for injecting at least one gas or reactive gas mixture (2), and optionally at least one gas or gas mixture (1) that is necessary for the pretreatment of the catalyst, via a switching valve (13), intermediate between said at least one system and the reactor, means for regulating and/or measuring the flow rate and composition of said liquid or liquid mixture, and said gas and/or gas mixture (8), downstream of the latter means, at least one means associated with the reactor for heating (15) said liquid or liquid mixture and/or said gas or mixture or mixture of gas and said liquid, at least one means for separation (23) of liquid and gaseous effluents withdrawn from the reactor after or at the same time as their condensation, if condensation is required, which allows for discontinuous sampling in which the liquid level and the sampling of gaseous and liquid effluents are managed by at least one valve (25) downstream of said at least one means for separation (23), downstream of the reactor, a switching valve (18) connecting the reactor (16) to said means for separation (23) and a reservoir (31), and at least one means to provide a regulation sequence that alternately ensures the accumulation and sampling of the liquid phase comprising:

said separator (23) for accumulating the liquid phase, and at least one collector of samples of liquid effluents (28) and means for discontinuously transferring the liquid phase from said separator (23) to said at least one collector of samples of liquid effluent (28), or optionally to said reservoir (31), said means for discontinuously transferring comprising said at least one valve (25), at least one collector of samples of gaseous effluents (36), that comprise or are associated with means for measuring the volumes of liquid and gas that are collected, at least one pressure regulation means, (33) directly coupled with said reservoir (31).

2. Equipment according to claim 1, characterized in that the reactor volume is between 0.1 and 20 $cm^3$.

3. Equipment according to claim 1, wherein a single means is used to carry out the condensation and separation of the effluents of the reactor.

4. Equipment according to claim 1, comprising said separation wherein the volume of the separator is between 0.1 and 20 $cm^3$.

5. Equipment according to claim 1, wherein the inside diameters of the reactor (16) is between 1 and 30 mm, and its length L is between 7 and 100 mm, such that the L/D ratio is greater than 2.

6. Equipment according to claim 5, wherein the L/D ratio is greater than 10.

7. Equipment according to claim 1, comprising said separation wherein the inside diameter of the separator is between 1 and 30 mm, and its length is between 1 and 1000 mm.

8. Equipment according to claim 1, further comprising means such that the reactor can operate at a pressure that is between atmospheric pressure and 35 MPa, a temperature of between 20° C. and 800° C., with a catalyst amount of between 0.01 and 20 $cm^3$, a liquid flow rate of between 0 and 100 gh-1, and a gas flow rate of between 0 and 5000 $cm^3$min-1.

9. The equipment of claim 1, wherein said reactor contains a catalyst.

10. The equipment according to claim 9, comprising at least one system for injecting a gas or gas mixture (1).

11. The equipment according to claim 1, further comprising at least one condensation means for condensing said gas.

12. The equipment according to claim 1, wherein the accumulation of liquid phase in said separator (23) is transferred to a reservoir (31).

13. The equipment according to claim 1, comprising at least one system for injecting a gas or gas mixture (2).

14. The equipment according to claim 1, comprising at least one means for heating (15) said liquid or liquid mixture.

* * * * *

UNITED STATES PATENT AND TRADEMARK OFFICE
CERTIFICATE OF CORRECTION

PATENT NO.   : 6,497,844 B1
DATED        : December 24, 2002
INVENTOR(S)  : Robert Bacaud et al.

It is certified that error appears in the above-identified patent and that said Letters Patent is hereby corrected as shown below:

<u>Title page, Item [54] and Column 1, line 1,</u>
Title, reads "EQUIPMENT FOR" should read -- EQUIPMENT AND --

<u>Title page,</u>
Item [75], Inventors, reads "Lyons" should read -- Lyon -- and reads "Briand" should read -- Fontainebleau --

<u>Column 12,</u>
Lines 35 and 43, reads "separation" should read -- separator --
Line 35, reads "diameters" should read -- diameter D --
Line 38, reads "between 7" should read -- between 1 --
Line 52, reads "cm3min-1" should read -- cm3.min-1 --

Signed and Sealed this

Nineteenth Day of August, 2003

JAMES E. ROGAN
*Director of the United States Patent and Trademark Office*